United States Patent [19]

Ruike

[11] Patent Number: 5,273,043
[45] Date of Patent: Dec. 28, 1993

[54] MEDICAL IMAGING APPARATUS WITH ACCURATE PATIENT POSTIONING

[75] Inventor: Toshikatsu Ruike, Tochigi, Japan

[73] Assignee: Kabushiki Kaisha Toshiba, Kawasaki, Japan

[21] Appl. No.: 691,518

[22] Filed: Apr. 25, 1991

[30] Foreign Application Priority Data

Apr. 27, 1990 [JP] Japan .................. 2-114856
Apr. 27, 1990 [JP] Japan .................. 2-114857

[51] Int. Cl.$^5$ ............................................ A61B 5/04
[52] U.S. Cl. ................................ 128/659; 378/209; 128/653.1
[58] Field of Search ................ 606/241, 242; 128/653.1, 653.5; 324/307, 309; 378/20, 163-164, 170, 195, 205-208

[56] References Cited

U.S. PATENT DOCUMENTS

| | | | |
|---|---|---|---|
| 3,974,388 | 8/1976 | Distler et al. | 378/20 |
| 4,017,737 | 4/1977 | Hudson et al. | 250/453 |
| 4,097,746 | 6/1978 | Ingham et al. | 378/20 |
| 4,296,329 | 10/1981 | Mirabella | 378/206 |
| 4,602,622 | 7/1986 | Bär et al. | 128/653.1 |
| 4,638,252 | 1/1987 | Bradshaw | 128/653.5 |
| 4,727,328 | 2/1988 | Carper et al. | 128/653.5 X |
| 4,771,785 | 9/1988 | Duer | 128/653.5 |
| 4,915,112 | 4/1990 | Singer | 128/653.1 |
| 4,922,915 | 5/1990 | Arnold et al. | 128/653.1 |
| 4,930,509 | 6/1990 | Brisson | 128/24 EL |

FOREIGN PATENT DOCUMENTS 0135161 3/1985 European Pat. Off. .

Primary Examiner—Francis Jaworski
Attorney, Agent, or Firm—Finnegan, Henderson, Farabow, Garrett & Dunner

[57] ABSTRACT

A medical imaging apparatus in which an easy and accurate positioning of an imaging target inside a patient within a view field of an imaging device is possible. The apparatus includes: a signal detector for collecting the image data, having a limited effective view field located inside a frame; a carrier for carrying the patient into the frame in order to place the imaging target portion of the patient within the effective view field of the signal detector; and an indication marking, attached on the carrier, for indicating a range on the carrier which can be located within the effective view field of the signal detector. The apparatus may further includes: a height adjustment device for adjusting a height of the carrier by moving the carrier in a vertical direction; and a height indicator for indicating the height of the carrier on a scale provided on a horizontal plane so as to provide an easily and accurately readable indication of the height of the carrier.

9 Claims, 11 Drawing Sheets

MEDICAL IMAGING APPARATUS WITH ACCURATE PATIENT POSTIONING

BACKGROUND OF THE INVENTION

1. Field of the Invention

The present invention relates to a medical imaging apparatus, such as a SPECT (Single Photon Emission Computed Tomography) apparatus, an X-ray CT (Computed Tomography) apparatus, and a gamma camera apparatus, in which a patient on a bed is positioned inside an imaging space defined by a view field of a signal detector for collecting imaging signals to be reconstructed into the images by using signal processing.

2. Description of the Background Art

One example of a conventional medical imaging apparatus is a SPECT apparatus which is a type of a gamma camera apparatus in which a gamma camera for detecting gamma rays through a fan beam collimator from a patient is provided around the patient to which an injection containing a radioactive isotope (RI) had been given, and fan beam tomographic image data for reconstructing tomographic images by using signal processings are collected by rotating the gamma camera around the patient for 360°. The gamma camera of such a SPECT apparatus has a two-dimensional detection capability so that multi-slice tomographic images can be obtained from a single 360° rotation of the gamma camera.

An exemplary configuration of such a conventional SPECT apparatus is shown in FIG. 1, where the SPECT apparatus generally comprises: a bed 6 for carrying a lying patient 9 with a head portion 9a supported by a head rest 1; and a frame 4 having a cylindrical bore 5 into which the patient 9 on the bed 6 is positioned by moving in a horizontal X direction, and a gamma camera 2 capable of rotating 360° around a circumference of the cylindrical bore 5 to collect the tomographic image data. The gamma camera 2 has an effective view field vf in the X direction which is narrower than its full width, and is capable of collecting tomographic image data only within this effective view field vf. The collected tomographic image data are subsequently reconstructed into the multi-slice tomographic images by using the signal processings, and the reconstructed tomographic images are displayed on a display device for medical diagnostic use. Here, the tomographic images can cover only those regions of the patient which are located within the effective view field vf of the gamma camera 2.

Such a SPECT apparatus has increasing demands because it is more useful in the diagnosis of a head portion and a heart portion compared with other diagnostic devices.

However, such a conventional SPECT apparatus has been associated with a problem that an accurate positioning of a target region of the patient within the effective view field vf of the gamma camera 2 has been difficult such that a re-positioning of the patient in the cylindrical bore 5 has often been necessary. This is due to the fact that a simple way of ascertain a correct positioning of the patient before the positioning of the patient inside the cylindrical bore 5 has not been available in a conventional SPECT apparatus such that the positioning of the patient has been depending on an experienced guess of an operator which may not necessarily be so reliable. Thus, the operator of a conventional SPECT apparatus has been required to put up with frequent and cumbersome repositioning of the patient.

Moreover, as already mentioned above, the SPECT apparatus is employed mostly for the diagnosis of the head portion of the patient, so that a capability for an easy and accurate positioning of a small and invisible part of the head portion of the patient is an important requirement in view of a maneuverability of the apparatus. For example, as shown in FIG. 2, a cerebellum portion 11 inside the head portion 9a of the patient 9 has been difficult to position accurately within the effective view field vf of the gamma camera 2 by a single patient positioning operation in a conventional SPECT apparatus.

Another example of a conventional medical imaging apparatus is an X-ray CT apparatus which has a typical configuration as shown in FIGS. 3 and 4.

This X-ray CT apparatus generally comprises: a bed 31 for carrying a lying patient 33, including a carrier plate 36 for moving the patient 33 in a horizontal X direction and a height adjustment unit 37 for adjusting a height of the carrier plate 36 in a vertical Z direction; and a frame 32 having a cylindrical bore 38 into which the patient 33 on the bed 31 is positioned by moving the carrier plate 36 in the horizontal X direction, an X-ray imaging unit including an X-ray tube 34 and a detector 35 which are capable of rotating 360° around a circumference of the cylindrical bore 38 to collect the tomographic image data.

As shown in FIG. 4, the X-ray tube 34 and the detector 35 are located at opposing positions on a slicing plane SP, and are rotated together on this slicing place SP around the patient 33 positioned inside the cylindrical bore 38 during the imaging process.

Now, in such a conventional X-ray CT apparatus, the height of the carrier plate 36 is made to be adjustable by means of the height adjustment unit 37 such that the apparatus can be adjusted to a patient of any physical size.

In adjusting the height of the carrier plate 36 by using the height adjustment unit 37, it is necessary to provide a height indicator for indicating a present height of the carrier plate 36 to an operator.

Conventionally, such a height indicator has been provided as shown in FIGS. 5(A) and 5(B). Namely, the height adjustment unit 37 of FIGS. 5(A) and 5(B) comprises: a fixed lower frame 51 fixed to the floor; a movable upper frame 52 on which the carrier table 36 is mounted and which is capable of moving in the vertical Z direction with respect to the fixed lower frame 51 by being driven by a power source (not shown); a scale 53 attached on a side of the fixed lower frame 51 along the vertical Z direction; and a pointer 54 attached on the same side of the movable upper frame 52 along the scale 53 which points a marking on the scale 53 corresponding to the height of the carrier plate 36 which can be read off by the operator.

However, in this configuration of the height adjustment unit 37 of FIGS. 5(A) and 5(B), the scale 53 is located at such a position that the operator has to bend down in order to read off the scale reading correctly, so that the reading operation is cumbersome. Also, in this configuration, a range of the adjustable heights for the carrier plate 36 is limited by a size of the scale 53, so that it has been difficult to lower the carrier plate 36 as low as considered preferabl  v many operators nowadays.

Alternatively, a heigh. indicator can also be provided as shown in FIGS. 6(A) and 6(B). Namely, the height adjustment unit 37 of FIGS. 6(A) and 6(B) comprises: a base frame 61 fixed to the floor; a movable frame 62 on which the carrier table 36 is mounted and which is capable of moving in the vertical Z direction with respect to the fixed lower frame 61 by being driven by a power source (not shown); a wire 64 suspended from the movable frame 62 in the vertical Z direction; a position detector 65 such as an encoder or a potentiometer which is attached on the wire 64 and measuring a length of the wire 64 corresponding to the height of the carrier plate 36; a drum 66 for rolling up or down the wire 64 as the movable frame 62 is lowered or raised; and a digital indicator using LED for indicating the height of the carrier plate 36 measured by the position detector 65 which is located on a side of the movable frame 62, such that the indication of the height can be read off easily and accurately.

However, in this configuration of the height adjustment unit 37 of FIGS. 6(A) and 6(B), numerous additional electronic components are required, so that the configuration of the height adjustment unit 37 becomes complicated and the apparatus inevitably becomes more expensive.

SUMMARY OF THE INVENTION

It is therefore an object of the present invention to provide a medical imaging apparatus in which an easy and accurate positioning of an imaging target inside a patient within a view field of an imaging device is possible.

It is also an object of the present invention to provide a medical imaging apparatus in which the indication of the height of the carrier plate can be read off easily and accurately without a complicated configuration and an increased cost.

According to one aspect of the present invention there is provided a medical imaging apparatus for obtaining images of an imaging target portion of a patient from image data collected from the patient, comprising: signal detector means for collecting the image data, having a limited effective view field located inside a frame; carrier means for carrying the patient into the frame in order to place the imaging target portion of the patient within the effective view field of the signal detector means; and indication marking means, attached on the carrier means, for indicating a range on the carrier means which can be located within the effective view field of the signal detector means.

According to another aspect of the present invention there is provided a medical imaging apparatus for obtaining images of an imaging target portion of a patient from image data collected from the patient, comprising: signal detector means for collecting the image data, having a limited effective view field located inside a frame; carrier means for carrying the patient into the frame in order to place the imaging target portion of the patient within the effective view field of the signal detector means; height adjustment means for adjusting a height of the carrier means by moving the carrier means in a vertical direction; and height indicator means for indicating the height of the carrier means adjusted by the height adjustment means on a scale provided on a horizontal plane.

Other features and advantages of the present invention will become apparent from the following description taken in conjunction with the accompanying drawings.

DETAILED DESCRIPTION OF THE PREFERRED EMBODIMENTS

Figure 1:
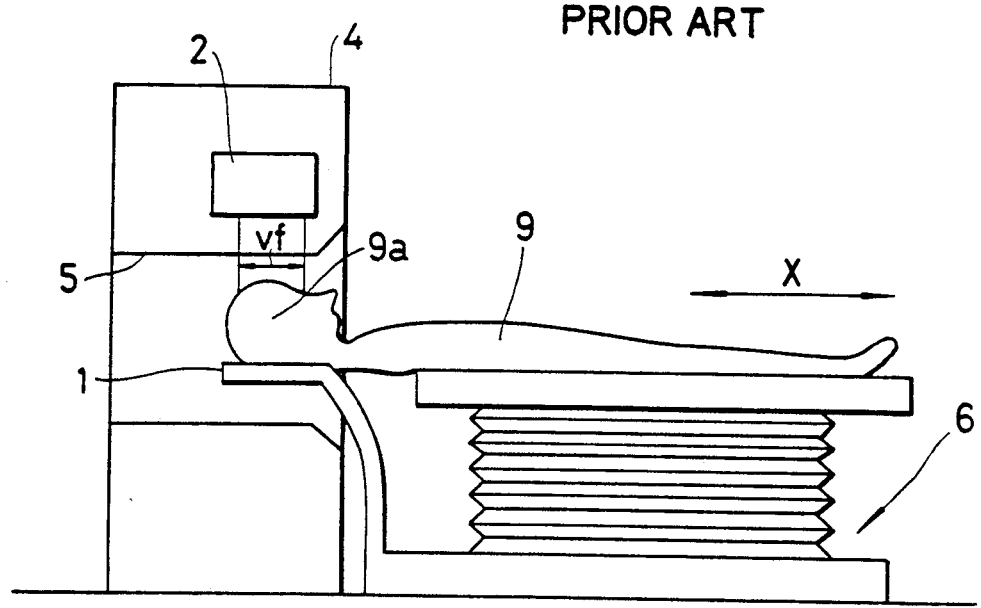
FIG. 1 is a schematic diagram of an example of a conventional SPECT apparatus.
Figure 2:
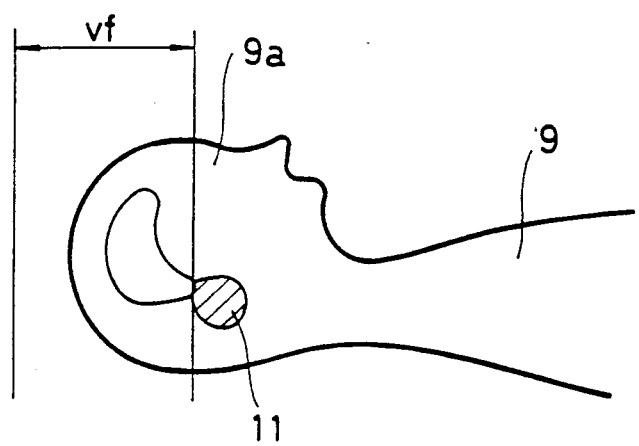
FIG. 2 is a schematic diagram for explaining the positioning of a patient in the conventional SPECT apparatus of FIG. 1
Figure 3:
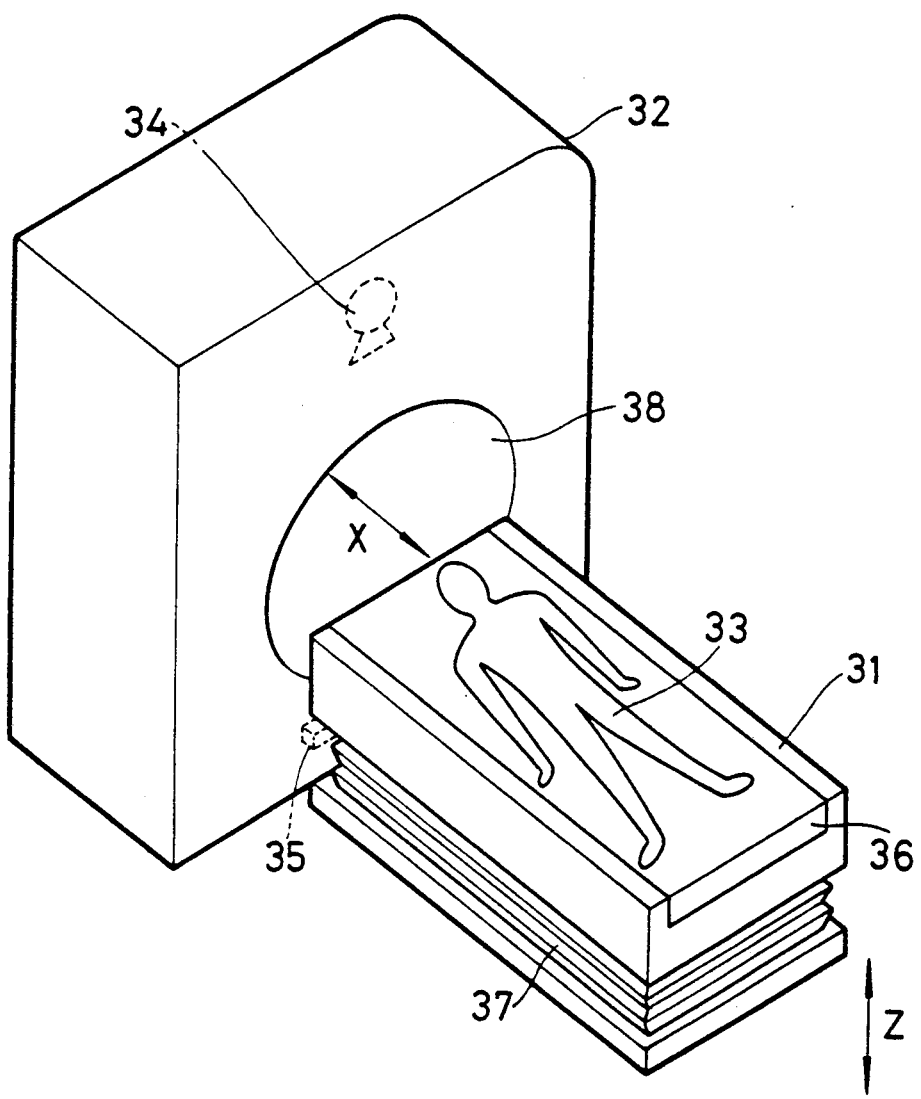
FIG. 3 is a schematic perspective view of an example of a conventional X-ray CT apparatus.
Figure 4:
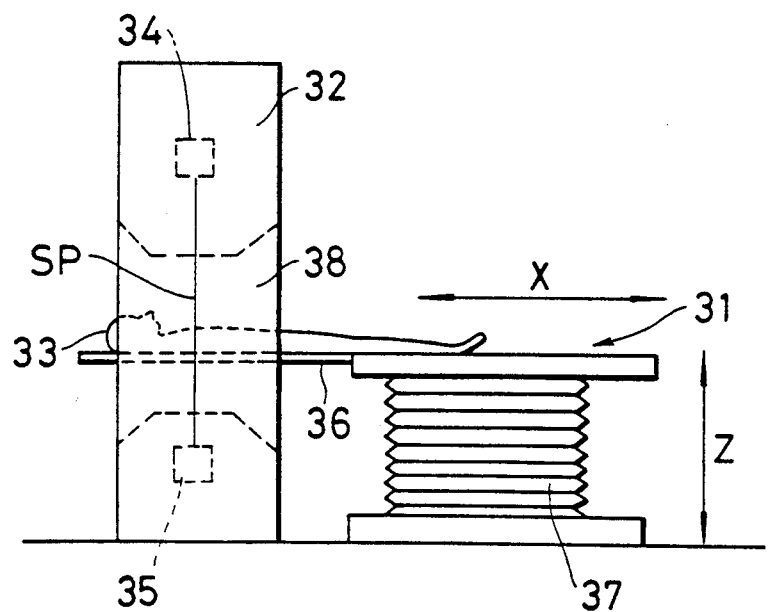
FIG. 4 is a schematic diagram of the conventional X-ray CT apparatus of FIG. 3.
Figure 5A:
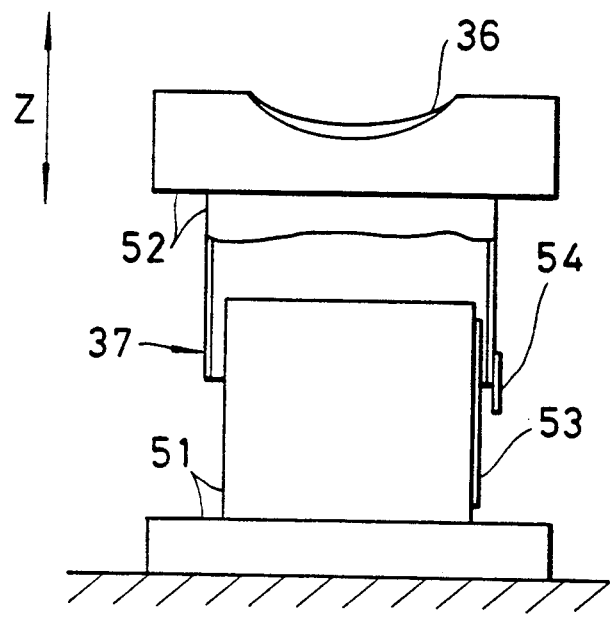
FIGS. 5(A) and 5(B) are a front view and a partial side view, respectively, of one example of a height adjustment unit in the conventional X-ray CT apparatus of FIG. 3.
Figure 5B:
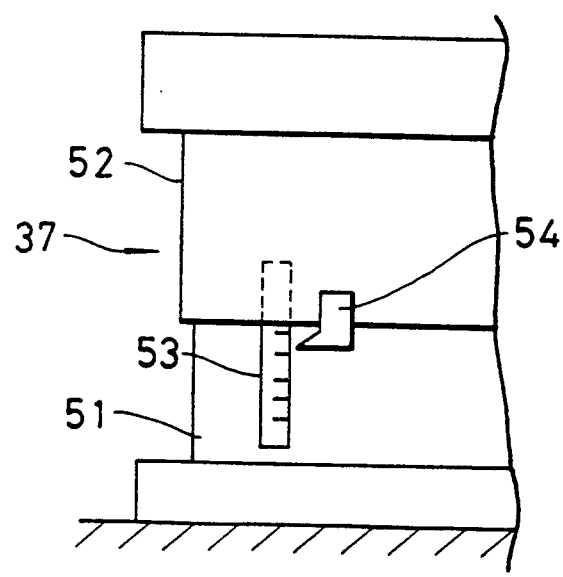
Figure 6A:
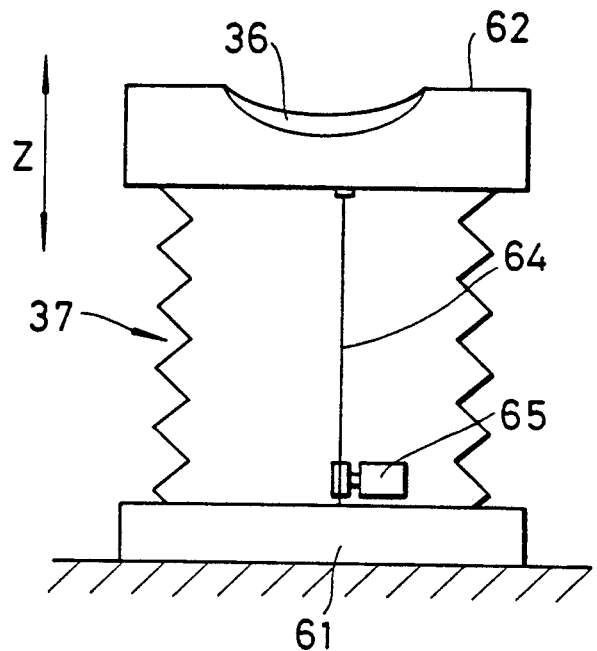
FIGS. 6(A) and 6(B) are a front view and a partial side view of another example of a height adjustment unit in the conventional X-ray CT apparatus of FIG. 3.
Figure 6B:
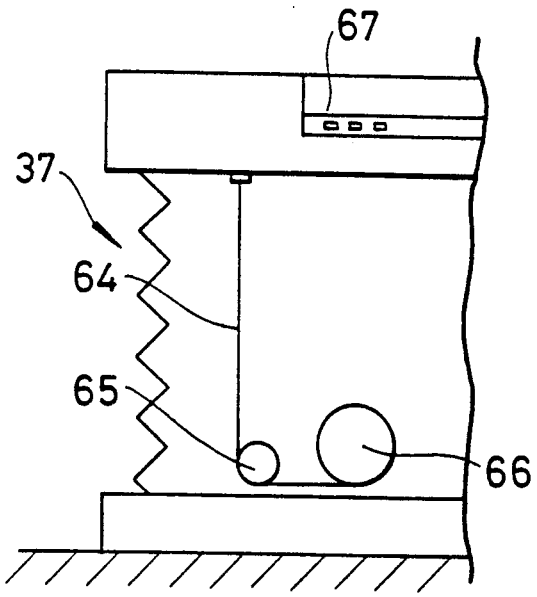
Figure 7:
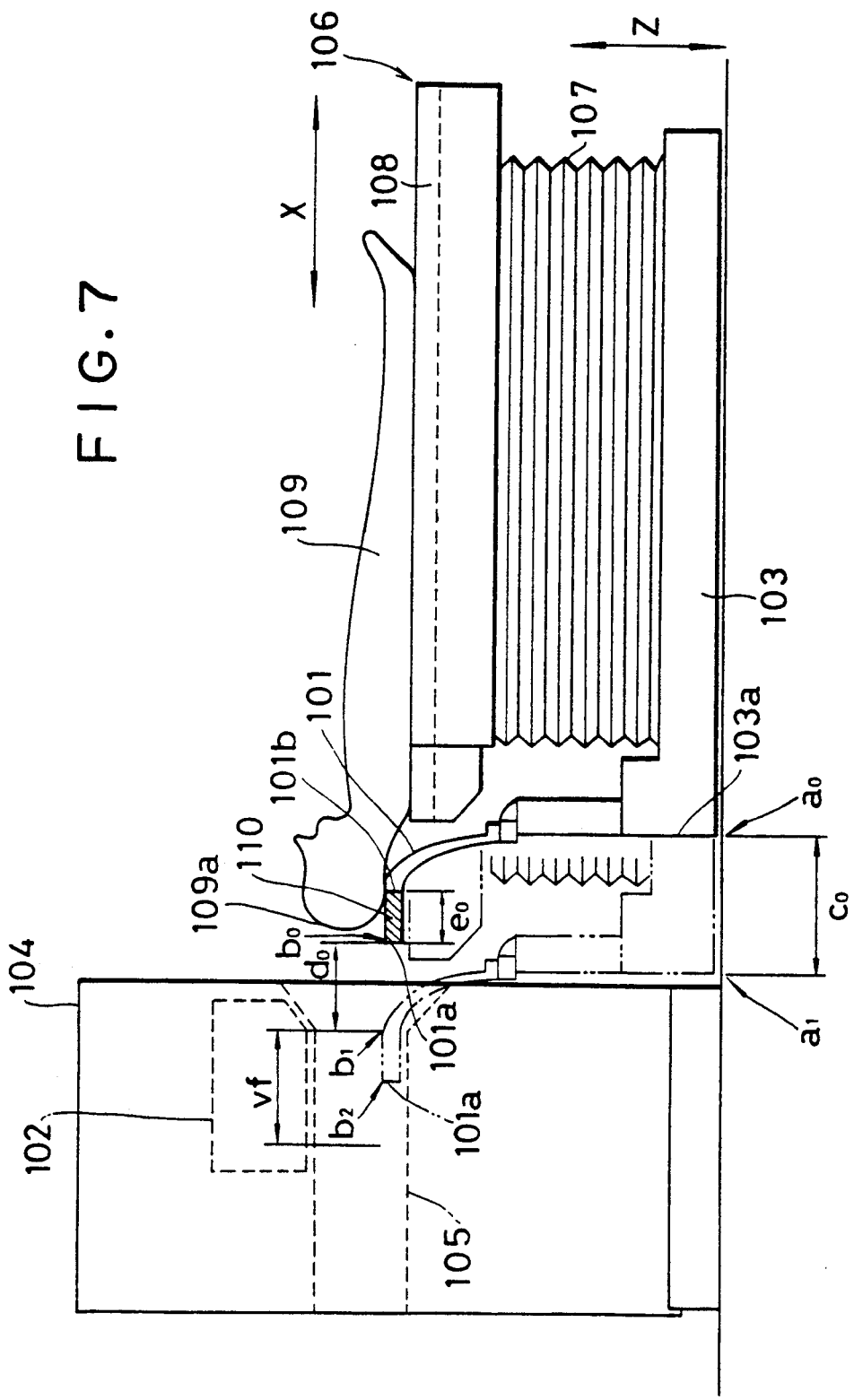
FIG. 7 is a schematic diagram of the first embodiment of a medical imaging apparatus according to the present invention.

Referring now to FIG. 7, a first embodiment of a medical imaging apparatus according to the present invention will be described.

In this embodiment, the apparatus comprises: a bed 106 including a carrier plate 108 for carrying a lying patent 109, a height adjustment unit 107 for supporting the carrier plate 108 at a freely adjustable height in a vertical Z direction, a common base 103 for supporting the height adjustment unit 107 in a state of being movable in a horizontal X direction, and a head rest 101 for supporting a head portion 109a of the patient 109 which is fixed to the common base 103; and a frame 104 having a cylindrical bore 105 into which the patient 109 on the bed 106 is positioned by moving in a horizontal X direction, and a gamma camera 102 capable of rotating 360° around a circumference of the cylindrical bore 105 to collect the tomographic image data. The gamma camera 102 has an effective view field vf in the X direction which is narrower than its full width, and is capable of collecting tomographic image data only within this effective view field vf. The collected tomographic image data are subsequently reconstructed into the multi-slice tomographic images by using the signal processings, and the reconstructed tomographic images are displayed on a display device for medical diagnostic use. Here, the tomographic images can cover only those regions of the patient which are located within the effective view field vf of the gamma camera 102.

A front end 103a of the common base 103 facing the frame 104 is initially located at a position $a_\phi$ before the imaging operation, and after the patient 109 is positioned on the bed 106, the bed 106 is moved in the horizontal X direction by a distance $c_\phi$ such that the front end 103a of the common base 103 is moved to a position $a_1$, while a front end 101a of the head rest 101 which is initially located at a position $b_\phi$ is also moved along with the common base 103 in the horizontal X direction into the cylindrical bore 105 of the frame 104. Here, the front end 101a of the head rest 101 enters the effective view field vf of the gamma camera 102 as it passes a position $b_1$ located at a distance $d_\phi$ away from the initial position $b_\phi$ and is moved further to a position $b_2$ located inside the effective view field vf of the gamma camera 102 at which the imaging operation is carried out.

Therefore, a range of positions located between the positions $b_1$ and $b_2$ which is equal to a length $e_\phi = c_\phi - d_\phi$ is going to be located within the effective view field vf of the gamma camera 102 in this apparatus.

Accordingly, the apparatus further includes an indication marking 110 of a length $e_\phi$ attached on a side of the head rest 101 from the front end 101a to a position 101b, which indicates this range that can be located within the effective view field vf of the gamma camera 102. This indication marking 110 can be formed in any easily recognizable appearance such as a printed line, a colored tape, or a plate attachment.

Thus, in this embodiment, the accurate positioning of an imaging target portion of the patient 109 within the effective view field vf of the gamma camera 102 can be achieved by a single positioning operation of simply adjusting the position of the patient 109 on the bed 106 with respect to the indication marking 110 before the patient 109 is moved into the imaging position inside the cylindrical bore 105 of the frame 104, and the bed 106 carrying the patient 109 can be moved toward the frame 104 only after the accurate positioning of the patient 109 is ascertained. Consequently, there is no need for frequent and cumbersome re-positioning of the patient 109 in this apparatus.

Figure 8:
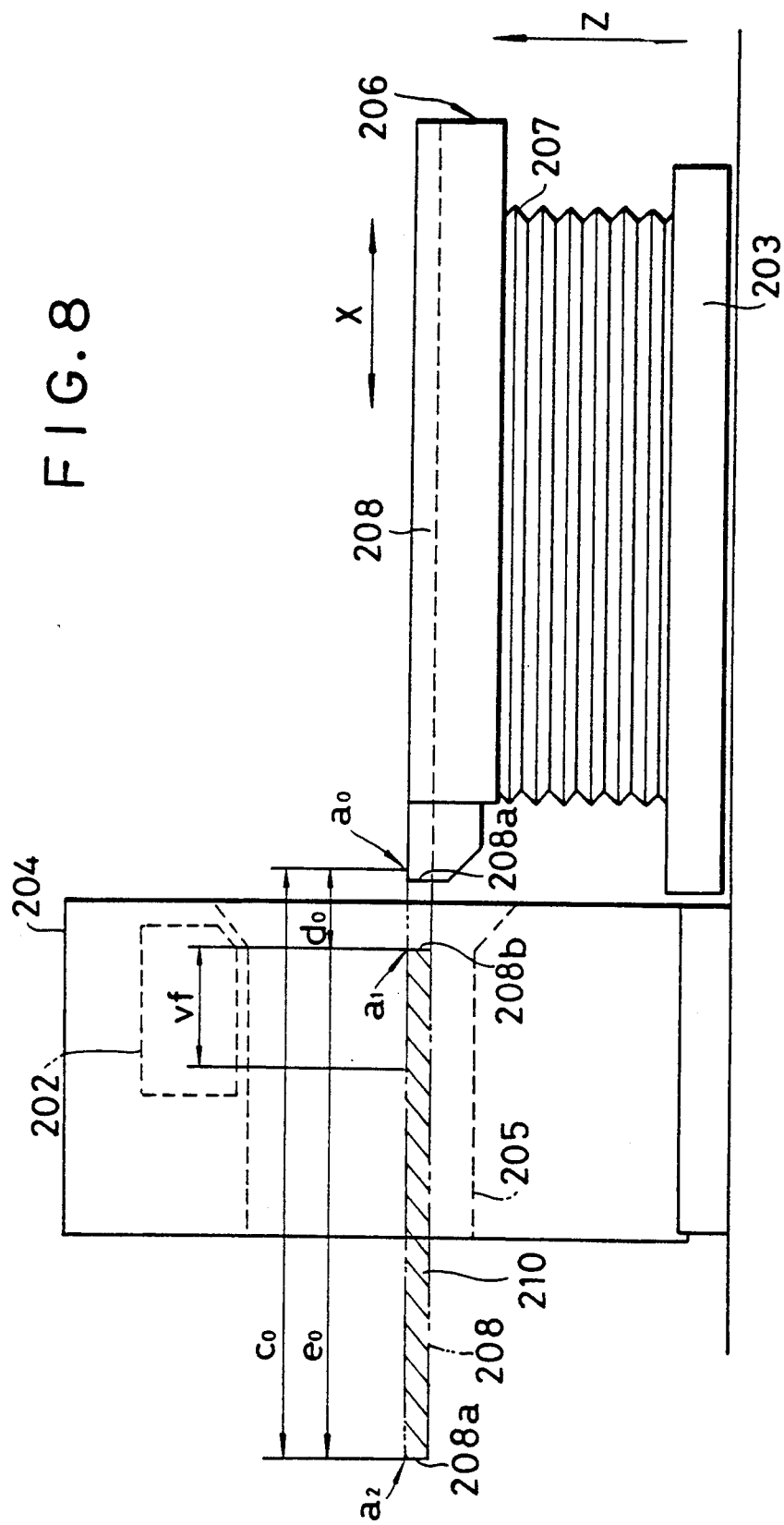
FIG. 8 is a schematic diagram of the second embodiment of a medical imaging apparatus according to the present invention.

Referring now to FIG. 8, a second embodiment of a medical imaging apparatus according to the present invention will be described.

In this embodiment, the apparatus comprises: a bed 206 including a carrier plate 208 for carrying a lying patient 209 in a state of being movable in a horizontal X direction, a height adjustment unit 207 for supporting the carrier plate 208 at a freely adjustable height in a vertical Z direction, a common base 203 for fixedly supporting the height adjustment unit 207; and a frame 204 having a cylindrical bore 205 into which the patient on the bed 206 is positioned by moving in a horizontal X direction, and a gamma camera 202 capable of rotating 360° around a circumference of the cylindrical bore 205 to collect the tomographic image data. The gamma camera 202 has an effective view field vf in the X direction which is narrower than its full width, and is capable of collecting tomographic image data only within this effective view field vf. The collected tomographic image data are subsequently reconstructed into the multi-slice tomographic images by using the signal processings, and the reconstructed tomographic images are displayed on a display device for medical diagnostic use. Here, the tomographic images can cover only those regions of the patient which are located within the effective view field vf of the gamma camera 202.

A front end 208a of the carrier plate 208 facing the frame 204 is initially located at a position $a_\phi$ before the imaging operation, and after the patient is positioned on the bed 206, the bed 206 can be moved in the horizontal X direction by a distance $c_\phi$ to a position $a_2$. Here, the front end 208a of the carrier plate 208 enters the effective view field vf of the gamma camera 202 as it passes a position $a_1$ located at a distance $d_\phi$ away from the initial position $a_\phi$.

Therefore, a range of positions located between the positions $a_1$ and $a_2$ which is equal to a length $e_\phi = c_\phi - d_\phi$ is going to be located within the effective view field vf of the gamma camera 202 in this apparatus.

Accordingly, the apparatus further includes an indication marking 210 of a length $e_\phi$ attached on a side of the carrier plate 208 from the front end 208a to a position 208b, which indicates this range that can be located within the effective view field vf of the gamma camera 202. This indication marking 210 can be formed in any easily recognizable appearance such as a printed line, a colored tape, or a plate attachment.

Thus, in this embodiment, the accurate positioning of an imaging target portion of the patient within the effective view field vf of the gamma camera 202 can be achieved by adjusting the position of the patient on the bed 206 with respect to the indication marking 210 before the patient is moved into the imaging position inside the cylindrical bore 205 of the frame 204, and the carrier plate 208 carrying the patient can be moved toward the frame 204 only after the accurate positioning of the patient is ascertained, as in the first embodiment described above.

Now, in the above embodiments of a medical imaging apparatus, the easily and accurately readable indication of the height of the carrier plate without a complicated configuration and an incresed cost can be provided by constructing the bed as in the following two embodiments.

Figure 9A:
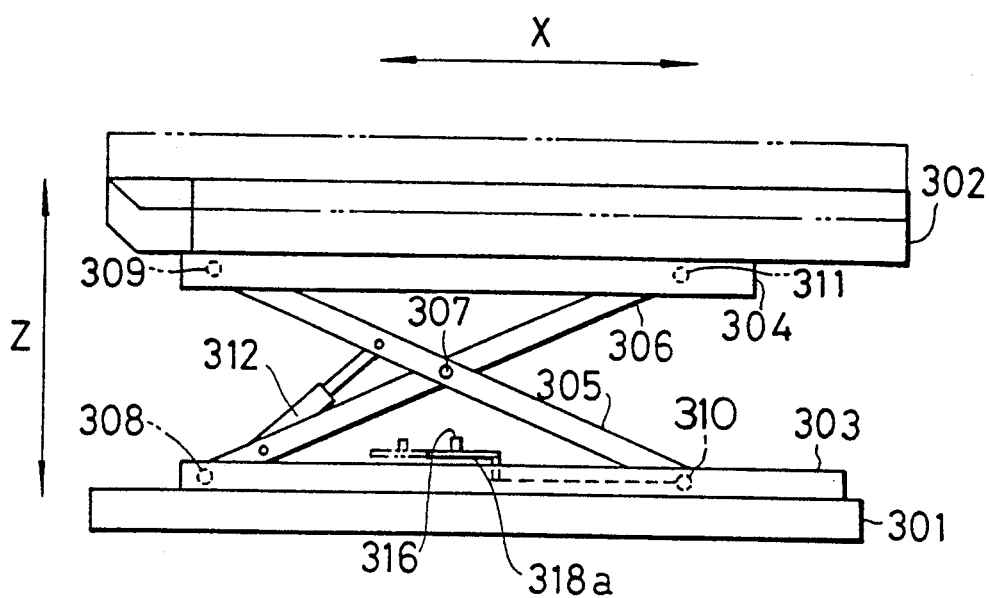
FIGS. 9(A) and 9(B) are a side view and a front view, respectively, of the first embodiment of a bed for a medical imaging apparatus according to the present invention.
Figure 9B:
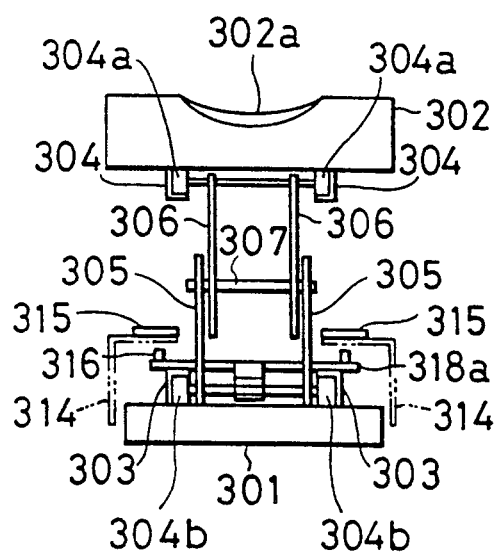

Referring now to FIGS. 9(A) and 9(B), a first embodiment of a bed for a medical imaging apparatus according to the present invention will be described.

In this embodiment, the bed comprises a base 301 having a lower rail 303 along an X direction; an upper frame 302 having a carrier plate 302a movable in the X direction on an upper surface, and an upper rail 304 running parallel to the lower rail 303 along the X direction on a lower surface; and a pair of mutually crossing links 305 and 306 for supporting the upper frame 302 over the base 301.

As shown in FIG. 9(A), the links 305 and 306 are held to be intersecting at a common pivot axis 307, where an upper end of the link 305 is rotatably fixed to an upper fixed axis 309 located at one end of the upper rail 304 and a lower end of the link 306 is rotatably fixed to a lower fixed axis 308 located at one end of the lower rail 303, while a lower end of the link 305 is rotatably connected to a lower slidable axis 310 located near the other end of the lower rail 303 through rollers 304b and an upper end of the link 306 is rotatably connected to an upper slidable axis 311 located near the other end of the upper rail 304 through rollers 304a.

The bed also includes a cylinder 312 connected between the links 305 and 306 on one side of the common pivot axis 307 such that the height of the upper frame 302 supported by the links 305 and 306 can be raised by the extension of the cylinder 312 in which case the lower and upper slidable axes 310 and 311 slide towards the lower and upper fixed axis 308 and 309 to raise the upper frame 302, or lowered by the contraction of the cylinder 312 in which case the lower and upper slidable axes 310 and 311 slides away from the lower and upper fixed axis 308 and 309 to lower the upper frame 302.

Figure 10:
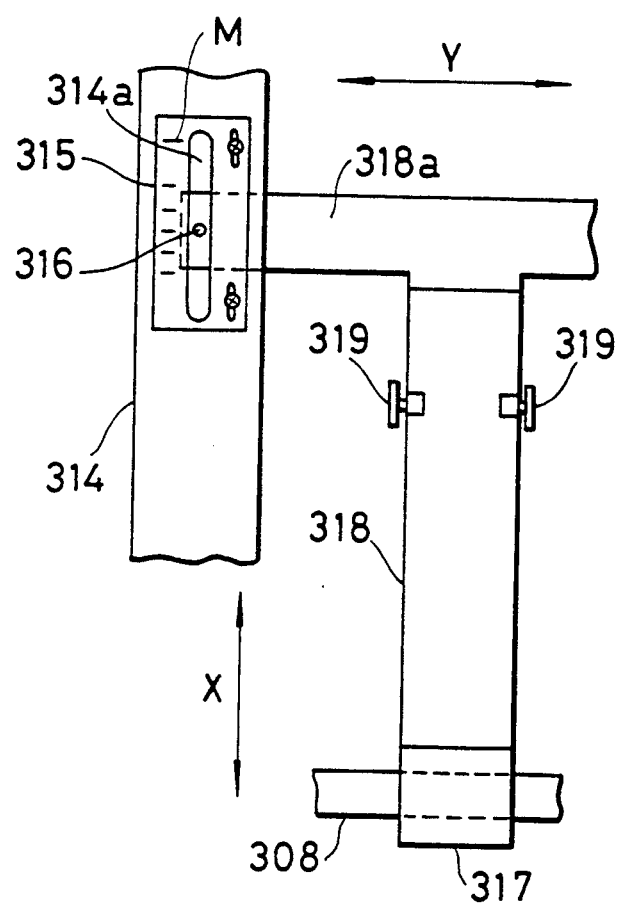
FIGS. 10(A), 10(B), and 10(C) are a top plan view, a front view, and a side view, respectively, of a main part of the bed of FIGS. 9(A) and 9(B).
Figure 10:
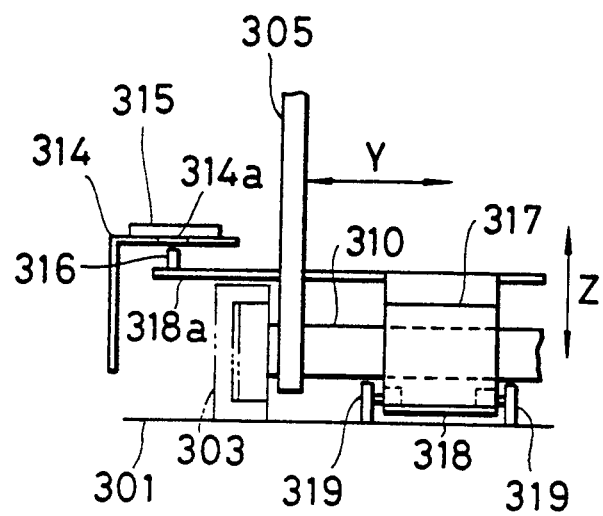
Figure 10:
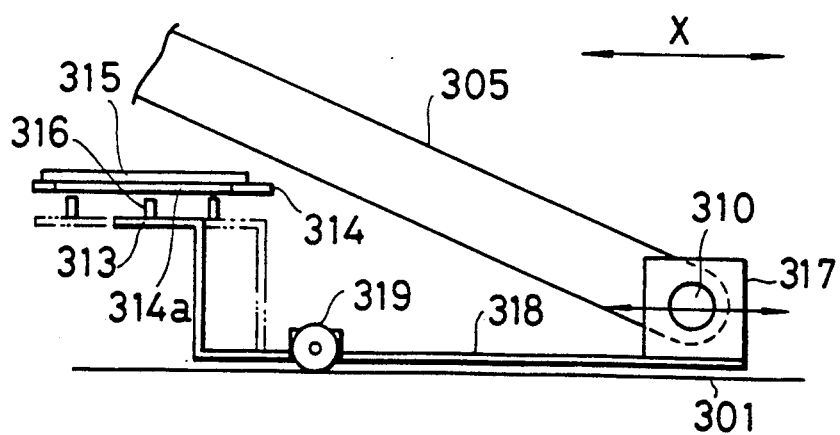

In addition, as shown in detail in FIGS. 10(A), 10(B), and 10(C), the bed also includes an arm member 318 extending in the X direction which is connected with the lower slidable axis 310 through a bearing member 317. The arm member 318 has a pointer support section 318a extending over the lower rail 303 in a Y direction on an end of which a pointer 316 pointing upwards is attached, and rollers 319 for supporting the arm member 318 on the base 301 at a position near the pointer support section 318a. Thus, as the lower slidable axis 310 slides in the X direction, the pointer 316 on the arm member 318 moves along the X direction for the same distance.

The bed further includes a cover 314 for covering over the pointer 316 on the arm member 318 which has a window 314a located directly above the pointer 316 such that the pointer 316 can be seen through the window 314a, and a scale cover 315 attached on the cover 314 which has a transparent region at least over the window 314a and a scale markings M for indicating the height of the carrier plate 302a on the upper frame 302 corresponding to the position of the pointer 316 in the X direction.

In this bed, by controlling the cylinder 312 from a control panel (not shown), the height of the upper frame 302 supported by the links 305 and 306 can be raised by the extension of the cylinder 312 in which case the lower and upper slidable axes 310 and 311 slide towards the lower and upper fixed axis 308 and 309 to raise the upper frame 302, or lowered by the contraction of the cylinder 312 in which case the lower and upper slidable axes 310 and 311 slides away from the lower and upper fixed axis 308 and 309 to lower the upper frame 302. Then, as the lower slidable axis 310 slides in the X direction, the pointer 316 on the arm member 318 moves along the X direction for the same distance, so that by reading the scale markings M on the horizontally provided scale cover 315 pointed by the pointer 316, the height of the carrier plate 302a on the upper frame 302 can be read off easily and accurately, without requiring a complicated configuration in the bed or a cumbersome operation to the operator. Also, because the indication of the height of the carrier plate 302a is provided on a horizontal plane, it is readily possible in this bed to lower the carrier plate 302a as low as considered preferable by many operators nowadays.

Figure 11A:
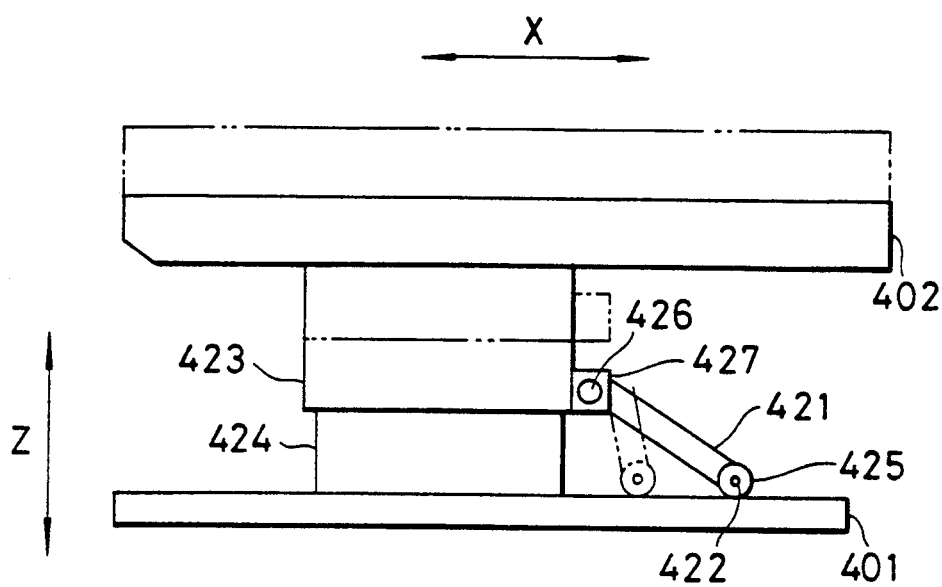
FIGS. 11(A) and 11(B) are a side view and a front view, respectively, of the second embodiment of a bed for a medical imaging apparatus according to the present invention.
Figure 11B:
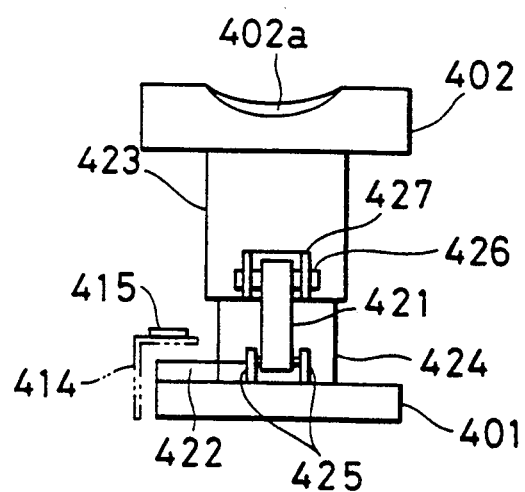

Referring now to FIGS. 11(A) and 11(B), a second embodiment of a bed for a medical imaging apparatus according to the present invention will be described.

In this embodiment, the bed comprises a base 401; a lower support frame 424 fixed on the base 401; an upper frame 402 having a carrier plate 402a movable in the X direction on an upper surface; an upper support frame 423 attached to a lower surface of the upper frame 402, which is movable in the Z direction with respect to the lower support frame 424 such that the height of the carrier plate 402a can be changed; and a link 421 having one end rotatably attached to one side of the upper support frame 423 through a shaft 426 and a bearing member 427 while the other end is equipped with rollers 425 for freely rolling on the base 401 in the X direction and a pointer 422 functioning as a rotational axis of the rollers 425.

The bed further includes a cover 414 for covering over the pointer 422 having a window (not shown) located directly above the pointer 422 such that the pointer 422 can be seen through the window, and a scale cover 415 attached on the cover 414 which has a transparent region at least over the window of the cover 414 and a scale markings M for indicating the height of the carrier plate 402a on the upper frame 402 corresponding to the position of the pointer 422 in the X direction.

In this bed, by controlling the upper support frame 423 from a control panel (not shown), the height of the upper frame 402 can be raised or lowered. Then, as one end of the link 421 is also raised or lowered along with the shaft 426 and the bearing member 427, the other end of the link 421 rolls on the base 401 such that the pointer 422 moves along the X direction. Thus, by reading the scale markings M on the horizontally provided scale cover 415 pointed by the pointer 422, the height of the carrier plate 402a on the upper frame 402 can be read off easily and accurately, without requiring a complicated configuration in the bed or a cumbersome operation to the operator. Also, because the indication of the height of the carrier plate 402a is provided on a horizontal plane, it is readily possible in this bed to lower the carrier plate 402a as low as considered preferable by many operators nowadays.

It is to be noted that the embodiments described above can be realized in any medical imaging apparatus of a type in which a patient on a bed is to be moved into a view field of a signal detector located inside a frame such as a SPECT apparatus, an X-ray CT apparatus, and a gamma camera apparatus.

Besides these, many modifications and variations of the above embodiments may be made without departing from the novel and advantageous features of the present invention. Accordingly, all such modifications and variations are intended to be included within the scope of the appended claims.

What is claimed is:

1. A medical imaging apparatus for obtaining images of an imaging target portion of a patient from image data collected from the patient, comprising:
    signal detector means for collecting the image data, having a limited effective view field located inside a frame;
    carrier means for carrying the patient from outside of the frame to inside of the frame in order to place the imaging target portion of the patient within the limited effective view field of the signal detector means; and
    indication marking means, attached on the carrier means, for indicating a range on the carrier means which can be located within the limited effective view field of the signal detector means which is visible while the carrier means is located outside of the frame.

2. The apparatus of claim 1, wherein the carrier means includes a head rest portion for supporting a head portion of the patient and the indication marking means is attached on the head rest portion of the carrier means.

3. The apparatus of claim 1, further comprising:
    height adjustment means for adjusting a height of the carrier means by moving the carrier means in a vertical direction; and
    height indicator means for indicating the height of the carrier means adjusted by the height adjustment means on a scale provided on a horizontal plane.

4. The apparatus of claim 3, wherein the height indicator means includes:

means for converting a vertical motion of the height adjustment means to move the carrier means in the vertical direction into a corresponding horizontal motion; and pointer means, connected with the converting means, for indicating the height of the carrier means by pointing the scale and changing a horizontal position with respect to the scale according to the corresponding horizontal motion.

5. The apparatus of claim 4, wherein the pointing means comprises a horizontally slidable member carrying out the corresponding horizontal motion, and the converting means comprises a link which is rotatably connected to a vertically moving part of the height adjustment means on one end and to the horizontally slidable member on another end.

6. A medical imaging apparatus for obtaining images of an imaging target portion of a patient from image data collected from the patient, comprising:

signal detector means for collecting the image data, having a limited effective view field located inside a frame;

carrier means for carrying the patient into the frame in order to place the imaging target portion of the patient within the effective view field of the signal detector means;

height adjustment means for adjusting a height of the carrier means by moving the carrier means in a vertical direction; and height indicator means for indicating the height of the carrier means adjusted by the height adjustment means on a scale provided on a horizontal plane.

7. The apparatus of claim 6, wherein the height indicator means includes:

means for converting a vertical motion of the height adjustment means to move the carrier means in the vertical direction into a corresponding horizontal motion; and pointer means, connected with the converting means, for indicating the height of the carrier means by pointing the scale and changing a horizontal position with respect to the scale according to the corresponding horizontal motion.

8. The apparatus of claim 7, wherein the pointing means comprises a horizontally slidable member carrying out the corresponding horizontal motion, and the converting means comprises a link which is rotatably connected to a vertically moving part of the height adjustment means on one end and to the horizontally slidable member on another end.

9. A system for obtaining a plurality of different tomographic images of radioisotopes given to an object, comprising:

detector means having a two-dimensional detection area for detecting gamma rays coming from the radioisotopes;

scanning means for causing a relative rotation around a rotation axis between the object and said detector means to obtain a plurality of projection data of a portion of said object corresponding to said detection area;

reconstructing means for reconstructing the tomographic images from said plurality of projection data;

carrier means for inserting said object into said scanning means along said rotation axis; and marking means disposed on said carrier means for visibly indicating a range along said rotation axis, where projection data are obtained when said object is sent to said scanning means by said carrier means.

* * * * *

UNITED STATES PATENT AND TRADEMARK OFFICE
CERTIFICATE OF CORRECTION

PATENT NO. : 5,273,043
DATED : December 28, 1993
INVENTOR(S) : Toshikatsu Ruike

It is certified that error appears in the above-indentified patent and that said Letters Patent is hereby corrected as shown below:

On the title page, Item [54] title of invention line 2 change "POSTIONING" to --POSITIONING--and column 1 line 3.

Abstract, line 4, change "includes" to --include--.

Signed and Sealed this

Fourth Day of October, 1994

Attest:

BRUCE LEHMAN

*Attesting Officer*   Commissioner of Patents and Trademarks